United States Patent [19]

Kraus et al.

[11] Patent Number: 4,576,589
[45] Date of Patent: Mar. 18, 1986

[54] TROCAR

[75] Inventors: Robert G. Kraus, Attleboro; Enora S. Kunica, Wellesley; Joseph J. Praderio, Quincy, all of Mass.

[73] Assignee: Codman & Shurtleff, Inc., Randolph, Mass.

[21] Appl. No.: 479,303

[22] Filed: Mar. 28, 1983

[51] Int. Cl.$^4$ .............................................. A61M 5/00
[52] U.S. Cl. ........................................ 604/8; 604/93; 604/161; 604/165; 128/DIG. 26
[58] Field of Search ..................... 604/8, 93, 117, 158, 604/160, 161, 164, 165, 166, 170, 175, 327, 328, 162, 171, 174, 177, 178, 179; 128/DIG. 26

[56] References Cited

U.S. PATENT DOCUMENTS

| | | | |
|---|---|---|---|
| 2,559,474 | 7/1951 | Son | 604/117 |
| 3,176,690 | 4/1965 | H'Doubler | 604/174 |
| 3,760,811 | 9/1973 | Andrew | 128/DIG. 26 |
| 3,827,434 | 8/1974 | Thompson | 604/160 |
| 4,192,305 | 3/1980 | Seberg | 604/174 |
| 4,209,015 | 6/1980 | Wicks | 604/174 |
| 4,231,367 | 11/1980 | Rash | 604/165 |
| 4,326,519 | 4/1982 | D'Alo et al. | 604/177 |
| 4,435,174 | 3/1984 | Redmond et al. | 604/174 |
| 4,445,893 | 5/1984 | Bodicky | 604/165 |

FOREIGN PATENT DOCUMENTS 2371204  7/1978  France .................. 604/164

*Primary Examiner*—C. Fred Rosenbaum
*Assistant Examiner*—Mark Rooney
*Attorney, Agent, or Firm*—Donal B. Tobin

[57] ABSTRACT

A trocar apparatus and method for introducing a drainage catheter into a drainage area of the body. The trocar includes a hollow cannula and a rod. The rod has a closed distal end and is longer than the cannula so that it can slide into the cannula and, when fully inserted, project a predetermined distance past the distal end of the cannula. The proximal ends of the cannula and the rod have respective supports which will contact one another to limit the forward motion of the rod into the cannula and an interfitting device cooperatively disposed on the supports to permit the user to hold the rod and the cannula in fixed relationship during insertion of the trocar. A catheter holder is placed on the cannula support. The projecting end of the rod is inserted into a drainage opening in the distal tip of the catheter, and a proximal portion of the catheter is held in the catheter holder, so that prior to insertion the catheter is aligned generally along the outside of the cannula. The flexible tip of the rod aligns itself generally along the axis of the catheter, so that during insertion the catheter presents a small cross-section to the tissue through which it is advancing. After the catheter is advanced to its desired position in the body, the rod is withdrawn into the cannula to free the distal tip of the catheter, the proximal portion of the catheter is released from the catheter holder, and then the cannula and the rod are removed from the body leaving the catheter in place.

11 Claims, 6 Drawing Figures

TROCAR

FIELD OF THE INVENTION

The present invention relates to a trocar, and more particularly to a method and apparatus for introducing a drainage catheter of the type used to drain excess liquid from a source region of the human body to a drainage region.

It is often necessary to drain excess fluid from one region of the body and deposit it in another region. Particularly in the condition known as hydrocephalus, the natural drainage system from the cranium fails to provide sufficient drainage, and it is necessary to drain excess fluid from the cranium in order to prevent damage to the brain. A particular system for carrying out this drainage is shown in U.S. Pat. No. 3,111,125 where there is shown a catheter extending from a burr hole in the skull into a ventricle region of the brain. Various fluid control apparatus may be connected to the exterior end of the catheter to provide a flow system for delivering the excess hydrocephalic fluid which is drained from the brain into other regions of the body, for example the heart or the abdominal cavity. U.S. Pat. No. 3,111,125 explains that various reservoir and flushing devices may be connected to the drainage catheter and secured under the scalp but outside the skull, and a drainage line may extend from the reservoir under the skin along the neck and across the chest cavity and then into the heart or abdominal cavity.

Several trocars are available for inserting the ventricular catheter into the desired region of the cranial cavity. Ventricular catheters are made of very flexible rubber-like material or plastic so that they will readily conform to the anatomy of the brain. One type of apparatus for inserting the catheter into the brain is a rigid stylet which is inserted through the lumen in the catheter to provide axial rigidity to the catheter. The catheter is placed on the stylet and then is inserted through a bore hole in the skull, through the brain into the ventricle and then the stylet is removed leaving the catheter in place. The catheter must then be anchored to the surrounding scalp or skull, and the desired additional fluid-control apparatus, like reservoirs and flushing devices, can then be attached to the catheter while it is in place. These reservoirs and anchoring devices cannot be attached prior to the insertion of the catheter by this stylet method, because, if the reservoir was attached to the proximal end of the catheter, it would not be possible to withdraw the stylet from the lumen of the catheter. Many surgeons prefer to assemble the entire drainage system before the operation is started in order to save time during the operative procedure. They also prefer to place the drainage line under the skin of the head, neck and chest and into the abdominal cavity or heart before the catheter is placed in the ventricle. In these instances, the use of the stylet method of catheter insertion is not the method of choice.

A split cannula trocar, similar to that shown in FIG. 1, has been used in the past to permit the ventricular catheter to be attached to its anchoring devices and the desired reservoir and flushing devices before the catheter is inserted into the ventricle of the brain. A split trocar as shown in FIG. 1 includes an axially extending cannula 10 with a sharpened distal tip 12. Split cannula 10 is a generally annular tube from which has been removed a circumferential segment along its entire axial length leaving an open slot 14 in the wall of the cannula. Disclike flange 16 with a corresponding slot 18 is affixed about a proximal portion of cannula 10 in a position outside the skull. Throughout this application the forward end of an apparatus will be called the distal end, and the rearward end which is disposed closer to the exterior of the body will be called the proximal end.

A solid nylon rod 20 with a distal tip 22 slides within the lumen of cannula 10. The proximal end 23 of rod 22 is enlarged for easy gripping by the user. Rod 20 is fully inserted into split cannula 10, and the entire device is then introduced through a burr hole in the skull and advanced through the brain tissue into the desired ventricle. The presence of rod 20 within split cannula 10 during insertion inhibits the entry of body tissue into the lumen of split cannula 10. When tip 12 of cannula 10 reaches its desired location within the brain, rod 20 is retracted completely out of split cannula 10 so that a ventricular catheter with its attached anchors, reservoirs and flushing devices may be inserted through the lumen of split cannula 10. When the distal end of the ventricular catheter reaches its desired position, split cannula 10 may be retracted completely out of the head leaving the ventricular catheter in place with its associated anchors, reservoirs and flushing devices in place. The surgeon need only suture the anchoring devices in place. Since the remainder of the fluid system has already been put in place, the operation is then complete.

Although the split trocar provides a perfectly acceptable way of introducing a ventricular catheter, the trocar must be larger than the catheter itself so that the catheter may be readily inserted through the lumen of the split cannula 10. It would be desirable to have a smaller trocar so that the introduction of the catheter would have less effect on the brain tissue. It would also be desirable to have a trocar in which the catheter did not have to be fed through the lumen of the cannula after the trocar was inserted but could instead be introduced to the brain at the same time as the trocar. It would also be desirable to have a device which could introduce the ventricular catheter at the same time that the cannula was inserted, while the anchoring reservoir and flushing devices were attached to the catheter.

SUMMARY OF THE INVENTION

The present invention provides a method and apparatus which embodies many of these desirable features. The trocar of the present invention includes a cannula having a lumen extending axially throughout its length and a rod having a closed distal end and a proximal end which may be slid into the cannula lumen. The rod is slightly longer than the cannula so that when the rod is fully inserted to the cannula, the distal end of the rod projects beyond the distal end of the cannula a predetermined distance.

First and second supports are fixed respectively to the proximal end portions of the cannula and the rod. A catheter holder is fixed to the cannula support for holding a proximal portion of the ventricular catheter. This catheter holder may include a longitudinal slot into which the catheter may be pressed and frictionally held. The distal end of the rod projects a predetermined distance past the distal end of the cannula when the rod is fully inserted to the cannula to provide a mechanism for holding the distal end of the ventricular catheter. It is well known that ventricular drainage catheters of the kind discussed in this invention have a series of holes at their distal end through which the fluid to be drained may enter the catheter. The projecting distal end of the rod may be inserted through one of these entry openings to hold the distal end of the catheter onto the insertion cannula. A proximal portion of the catheter is placed in the catheter holder on the cannula support so that the catheter extends from the distal tip of the trocar along the cannula, into the catheter holder and then out past the end of the trocar. This design permits anchoring, flushing and reservoir devices to be connected to the ventricular catheter before the catheter is inserted into the ventricle.

The support for the cannula and the rod abut against one another when the rod is fully inserted in the cannula to control the distance which the distal end of the rod extends beyond the distal end of the cannula.

First and second handles are fixed respectively to the cannula and the rod supports. An interfitting mechanism is placed on the first and second handles to provide a means for restraining the rod from receding into the cannula during insertion. The handles also provide a good grip for the user. Wings and raised projections may be added to further facilitate gripping.

In the preferred embodiment, the device for interfitting the cannula and the rod is a V-bed with a first part of the "V" mounted on the cannula and the second part of the "V" mounted on the rod. The V-bed interfitting system also provides a stop mechanism for controlling the distance the distal end of the rod projects beyond the distal end of the cannula.

The rod may be a flexible plastic monofilament having an outside circumferential surface which slides against the interior wall of the cannula lumen to substantially fill the lumen during cannula insertion to inhibit the entry of body tissue into the lumen. The rod has sufficient axial rigidity to slide easily into the cannula and to put some tension on the catheter when it is in place.

The present invention also provides a method for inserting a drainage catheter having a distal end with at least one drainage opening into a space of the body to be drained. For hydrocephalus, the method includes the steps of providing an opening in the skull then providing a trocar with a hollow cannula having a support and a catheter holder attached to the proximal end of the cannula. The trocar also includes a rod which may be slid into the lumen of the cannula and which has a length greater than the length of the cannula so that the distal end of the rod projects a predetermined distance beyond the end of the cannula when the rod is fully inserted. The rod also has a support affixed to its proximal end and a stop to control the predetermined distance that the distal end of the rod projects beyond the distal end of the cannula. The rod is fully inserted into the cannula. The projecting end of the rod is inserted through at least one of the holes in the distal end of the drainage catheter. The catheter is then aligned along the outside of the cannula and the proximal portion of the catheter is inserted into the catheter holder. The flexible rod tends to align itself along the axis of the catheter and vice versa, so that the rod and the catheter present a small cross-section to the tissue through which they advance. The rod has sufficient axial rigidity to put some tension on the catheter when it is in place on the tip of the rod and the catheter is stretched along the outside of the cannula and inserted in the catheter holder. The trocar and the catheter together are then inserted through the opening, and the distal end of the catheter is advanced into the desired position in the area to be drained. The rod is then retracted into the cannula to release the end of the catheter. The proximal portion of the catheter is then released from the catheter holder, and the entire trocar is then retracted outside the body. Alternatively, the rod may be entirely retracted before the cannula is retracted. In a further alternative, the end of the catheter may be connected to anchoring, reservoir and flushing devices prior to the insertion of the catheter.

BRIEF DESCRIPTION OF THE DRAWINGS

These and other advantages and features of the present invention will become apparent from the following description of certain embodiments taken in conjunction with the following drawings in which.

DETAILED DESCRIPTION OF THE PREFERRED EMBODIMENTS

Figure 1:
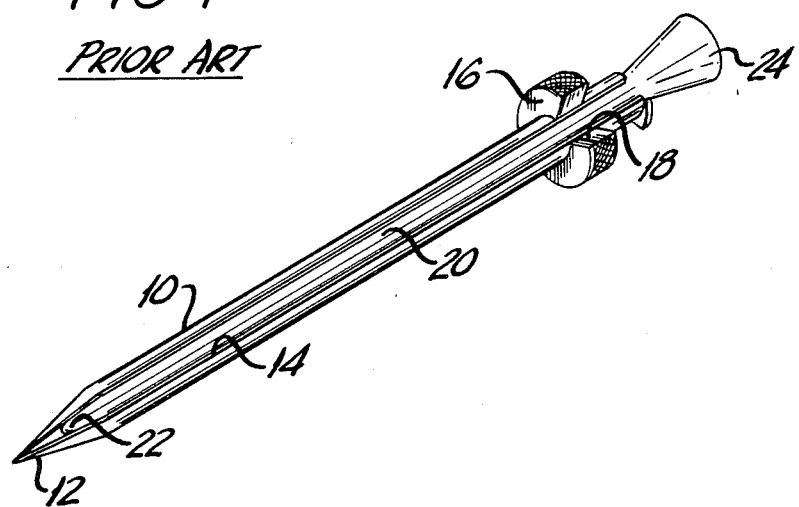
FIG. 1 shows a perspective view of a slotted trocar of the prior art.
Figure 2:
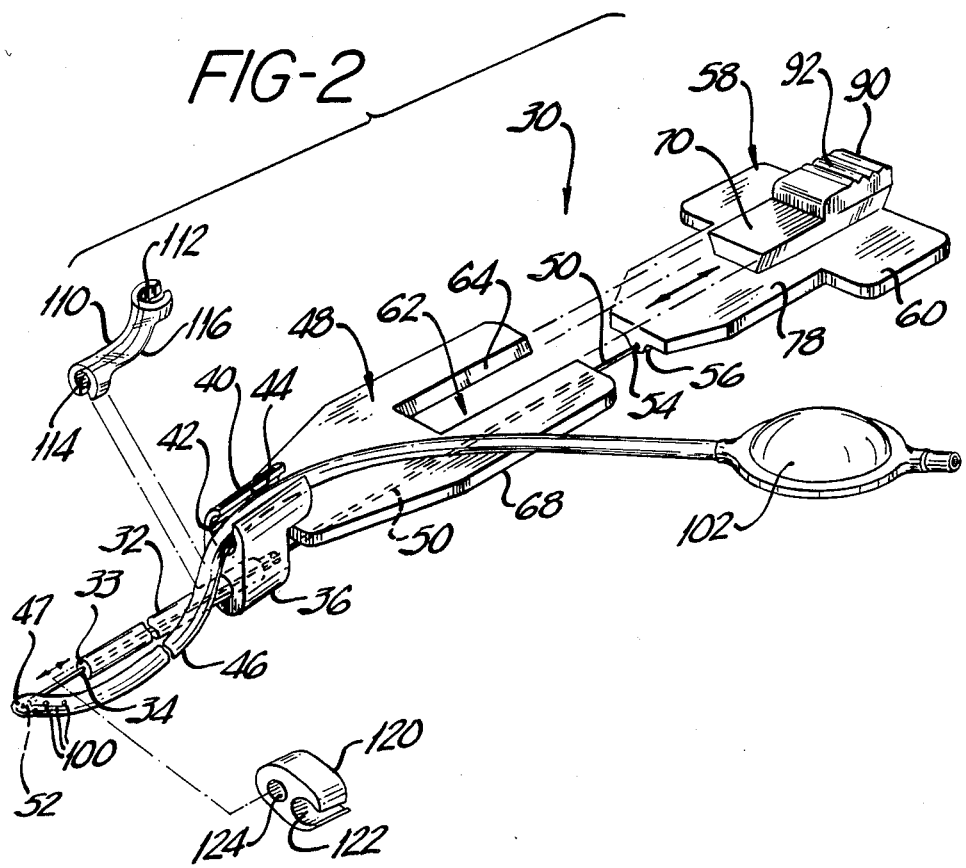
FIG. 2 shows an exploded perspective of the present trocar with a catheter in place and with a reservoir connected to the end of the catheter.
Figure 3:
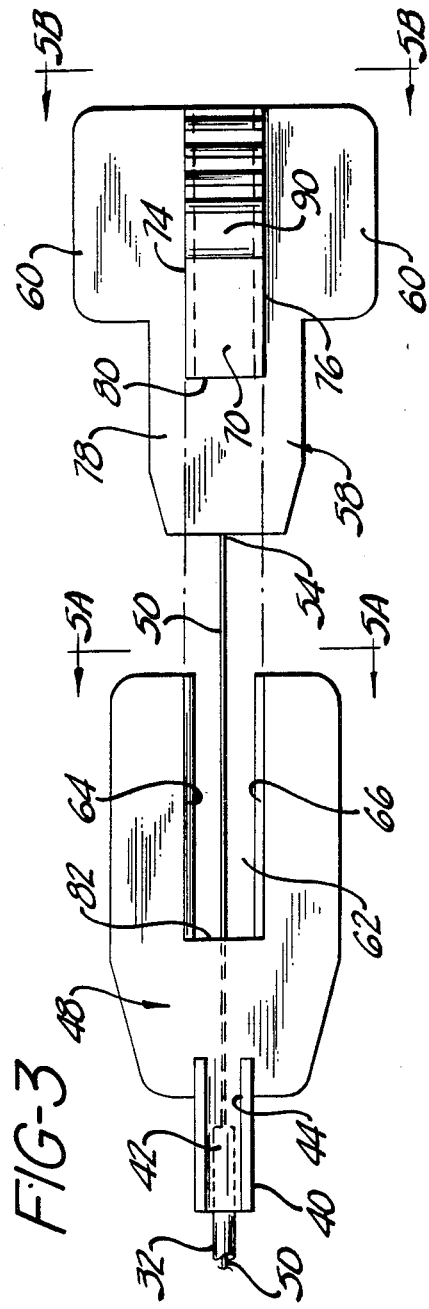
FIG. 3 shows a partial plan view of the apparatus shown in FIG. 2.
Figure 4:
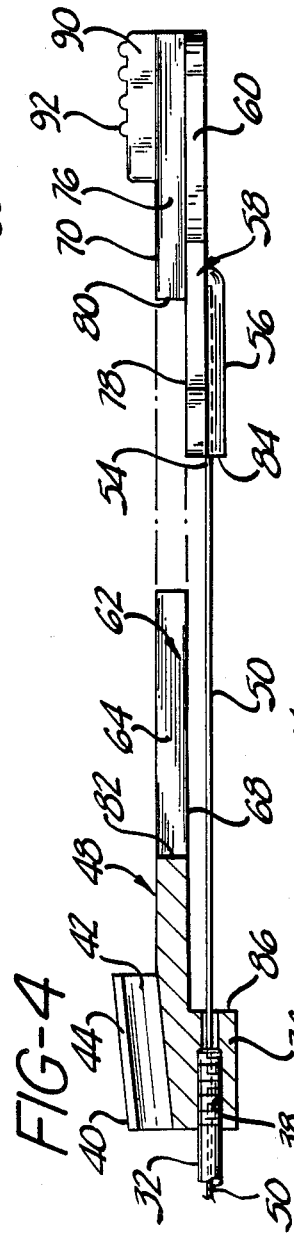
FIG. 4 shows a partial elevation view, partly in section, of the apparatus shown in FIG. 2.
Figure 5B:
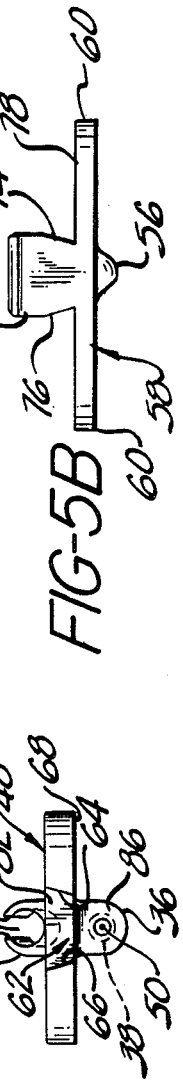
FIGS. 5A and 5B show end views of the apparatus shown in FIG. 3.
Figure 5A:

Referring now to FIG. 2, there is shown an exploded perspective view of the trocar 30 of the present invention with a ventricular catheter attached. Trocar 30 includes two basic parts. The first part includes a cannula 32 having a generally annular configuration with a lumen 34 extending through its length. Cannula 32 is made of a rigid material, preferably stainless steel. Cannula 32 is supported by support 36 into which the proximal end of cannula 32 is secured. As can be seen more clearly in FIG. 4, cannula 32 is mounted in a bore 38 in support 36, and bore 38 extends completely through support 36. Cannula 32 can be threaded or glued or otherwise secured into bore 38. A catheter holder 40 is mounted on support 36, preferably in an integral fashion. Holder 40 includes a generally axial, open slot 42 whose cross-section is generally circular. The open part of the slot is less than 180° of the circular cross-section so that the slot includes edges 44 which project into the space defining slot 42. Edges 44 are dimensioned to engage the outer periphery of a catheter 46 so as to frictionally hold catheter 46 in place on catheter holder 40.

Extending proximally from cannula support 36 is handle 48. Handle 48 is preferably a generally planar and rigid flange extending parallel to the axis of cannula 32 but offset radially a predetermined distance from the axis of cannula 32. Handle 48 provides an easy gripping means for the user. Although handle 48 is a desirable feature of the present invention, it is not required. Also, handle 48 need not be planar and need not be made of a completely rigid material.

The second principal part of the trocar of the present invention is a rod 50. Rod 50 is preferably a flexible, solid plastic monofilament with a circular cross-section. The rod has sufficient axial rigidity to put some tension on the catheter. However, rod 50 could be made of a variety of materials and could even be a multifilament or a tubular material with a closed, distal end. Rod 50 slides inside lumen 34 of cannula 32. The length of rod 50 is a predetermined distance slightly greater than the length of cannula 32 so that when rod 50 is completely inserted into cannula 32, the distal end 52 of rod 50 extends a predetermined distance beyond the distal end 33 of cannula 32. Rod 50 is preferably sized so that its outer circumferential surface slides along the interior wall of lumen 34, so that rod 50 substantially fills lumen 34 to inhibit the entry of body tissue into lumen 34 while trocar 30 is being inserted into place. The proximal end 54 of rod 50 is supported in rod support 56. Proximal end 54 of rod 50 is preferably glued into support 56. However, other means of affixing rod 50 into support 56 can be used. A rod handle 58 is preferably affixed to rod support 56. In the preferred embodiment, rod handle 58 is a generally planar, rigid flange and is used to facilitate gripping by a user. Handle 58 may also include wings 60 which project laterally beyond the edges of cannula handle 48 to further facilitate user handling.

Although it is desirable to include rod handle 58, it is not required, and rod handle 58 need not be planar and need not be made of a completely rigid material.

It is also desirable to include a device for interfitting rod 50 and cannula 32 to permit the user to more securely hold trocar 30 without permitting relative movement between cannula 32 and rod 50, and particularly to prevent rod 50 from receding into cannula 30 and releasing catheter 46 during insertion.

A preferred interfitting device includes a V-bed whose cooperating parts are mounted on handles 48 and 58, respectively. The V-bed is aligned generally axially with respect to cannula 32 so that the V-bed may interfit as rod 50 is slid into cannula 32.

The V-bed includes a U-shaped slot 62 in cannula handle 48 extending generally parallel to the axis of cannula 32 and symmetrically oriented about the axis of cannula 32. Slot 62 makes cannula handle 48 look like a generally symmetrical U-shaped flange. The confronting sidewalls 64 and 66 of slot 62 are aligned at equal and opposite angles to the plane perpendicular to planar cannula handle 48 preferably at about a 15° angle to the plane perpendicular to the plane of handle 48, although this angle is not critical. It is also not essential that these two angles be exactly the same but only that they have an opposite slope. Walls 64 and 66 form a first portion of a V-bed. Surface 68 of cannula handle 48 is a first mating surface which will be further described later in this application.

The second part of the V-bed is mounted on rod handle 58 includes projection 70 which extends generally perpendicular to the plane of rod handle 58. Projection 70 has opposite sidewalls 74 and 76 which form equal and opposite angles to the plan perpendicular to the surface of rod handle 58, so that projection 70 and its sidewalls 74 and 76 form the second portion of the V-bed interfitting device for rod handle 58 and cannula handle 48. The angle which sidewalls 74 and 76 form with the plane perpendicular to rod handle 58 is preferably about 15° but can be any convenient angle which mates with sidewalls 64 and 66 to form a V-bed.

Mating surface 78 of rod handle 58 mates with the mating surface 68 of cannula handle 48 in close sliding contact to provide further stability for the interfitting device which connects cannula handle 48 to rod handle 58. It can be seen that the V-bed, part of which is located on rod handle 58 and part of which is located on cannula handle 58, provides a convenient interfitting device for cannula 32 and rod 50 to permit the user to more securely hold trocar 30. As rod 50 is slid into cannula 32, the V-bed interfits. As will be explained later in the application, the user can grasp the V-bed firmly so that the distal end 52 of rod 50 will not recede into cannula 32 while trocar 30 is being inserted into the body so as not to release catheter 46 during insertion.

The distal wall 80 of projection 70 is aligned with and abuts against the proximally facing wall 82 of slot 62 to provide a stop limiting the forward motion of rod 50 through cannula 32. Alternatively, a stop may be provided by the contact of the distal portion 84 of rod support 56 against the proximal portion 86 of cannula support 36 to also provide a stop limiting the forward motion of rod 50 through cannula 32.

A raised portion 90 extends from projection 70 in the direction away from mating surface 78 and includes a plurality of transverse ridges 92 to facilitate gripping by the user.

In operation, the trocar of the present invention is used to insert a drainage catheter 46 which has a plurality of holes 100 in its distal end 47 through which the fluid to be drained enters catheter 46. Rod 50 is inserted into the proximal end of lumen 34 of cannula 32 and slid axially all the way through lumen 34 until the distal end 52 of rod 50 projects beyond the distal end 33 of cannula 32. The forward motion of rod 50 will stop when the distal end 84 of rod support 56 hits the proximal end 86 of cannula support 36 or alternatively when the distal wall 80 of projection 70 hits the proximal wall 82 of slot 62. As rod 50 slides into cannula 32, the cooperating V-bed portions of slot 62 and projection 70 will interfit and mating surfaces 68 and 78 will slide across one another to provide an interfitting device which will permit only axial motion of rod 50 with respect to cannula 32. The flanges which form cannula handle 48 and rod handle 58 provide a secure handle which can easily be grasped by the user.

Before trocar 30 is inserted into the body, cannula 46 is mounted on trocar 30 by inserting the distal end 52 of rod 50 into one of the drainage holes 100 on the tip of catheter 46. Preferably, rod 50 is inserted into the most distal drainage hole 100 on catheter 46. Rod 50 is somewhat flexible so that it will tend to align itself generally along the axis of catheter 46. Catheter 46 is also flexible so that it will tend to align itself generally axially of cannula 32. Rod 50 has sufficient axial rigidity to put some tension on catheter 46. Thus, the leading distal edge 47 of catheter 46 is aligned in such a way as to present a small cross-section to the tissue through which it advances to facilitate easy insertion into the body. By contrast, if rod 50 were inserted into a more proximally located drainage hole 100 of catheter 46, distal end 47 would extend transversely of cannula 32 and would present a somewhat larger cross-section. The body of catheter 46 is stretched along the outside of cannula 32. A proximal portion of catheter 46 is pressed into slot 42 of catheter holder 40 and held in position by edges 44 and placed under some tension. A reservoir 102 may be attached to the proximal end of catheter 46 before trocar 30 and 46 catheter are inserted into the body. In many cases, reservoir 102 and catheter 46 are formed integrally during their manufacturing process. The entire drainage system may be attached to catheter 46 and a drainage line may be placed under the skin along the side of the head, neck and chest, and the drainage line may be inserted into the heart or abdominal cavity before catheter 46 is inserted into the cranial cavity.

In an alternative embodiment, an anchoring clip 110 having a catheter holder slots 112 and 114 connected by bed 116, similar to holder slot 42, may be affixed to catheter 46 by attaching slot 114 about catheter 46 at a point between its distal end 47 and catheter holder 40. Slot 112 is often at a right angle to slot 114, so that when anchoring device 110 is placed against the outside surface of the skull catheter 46 may make a sharp right-angle turn as it exits from the skull and can be guided through slots 112 and 114 and along bed 116 to avoid kinking or crimping. This right-angle turn is important, because reservoir 102 is laid under the scalp along the outside surface of the skull, and the drainage end of the hydrocephalic fluid system is inserted under the skin along the side of the head, neck and chest and then into the heart or abdominal cavity.

Also provided, as shown in FIG. 2, is a sliding clip 120 with slot 122, similar to slot 42, for gripping catheter 46 and bore 124 which slides tightly onto cannula 32. Cannula 32 can be introduced through bore 124 and then catheter 46 can be pressed into slot 122. Clip 120 provides support for catheter 46 between its distal tip 47 and catheter holder 40 while the catheter is being inserted. Clip 120 can be attached to catheter 46 a carefully measured distance from distal tip 47 of catheter 46 so that the surgeon will know that the distal tip 47 of catheter 46 is placed in exactly the right location within the body.

With trocar 30 and catheter 46 assembled as previously described, trocar 30 and catheter 46 may be inserted through a hole previously made in the skull and advanced through the brain tissue into the desired location within the brain. The user holds cannula handle 48 and rod handle 58 sufficiently tightly to prevent rod 50 from receding into cannula 33 as it is advancing through the brain tissue. The large surface contact between mating surfaces 68 and 78 provide sufficient friction to prevent rod handle 58 and its associated rod 50 from receding as the distal end 47 of catheter 46 experience a resistance as it is advanced into the brain tissue.

After catheter 46 is advanced to its desired position within the brain, rod 50 is retracted to free distal end 47 of catheter 46. Rod 50 may be retracted partially into cannula 32 or it may be entirely removed from cannula 32, according to the preference of the user. If the rod is entirely removed before the cannula is removed, cerebrospinal fluid will drain from the cannula verifying correct placement of the catheter and permitting a sample of fluid to be obtained. The proximal end portion of catheter 46, which is held in slot 42 of catheter holder 40, is then released by the user, and cannula 32 is then retracted by grasping flange 48. It can be seen that trocar 30 can be completely retracted without interfering with the proximal end of catheter 46 or reservoir 102 or any other flushing or anchoring devices that may be associated with the proximal end of catheter 46.

In those instances where anchor 110 is placed on catheter 46 prior to insertion of catheter 46, anchor 110 need only be sutured in place to the scalp.

While the present invention has been described in connection with certain preferred embodiments, particularly relating to a ventricular catheter for the treatment of hydrocephalus, those skilled in the art will appreciate that certain modifications may be made without departing from the scope of the present invention and that the trocar and method of this invention could be used in other areas of the body. It is, therefore, not intended that the present invention be limited except as set forth in the following claims.

We claim:

1. A trocar comprising:
   a cannula having a lumen extending axially throughout its length and having a distal end and a proximal end;
   a generally U-shaped flange affixed to the proximal end of said cannula and aligned generally parallel to and radially offset from the longitudinal axis of said cannula;
   said U-shaped flange including a first mating surface, and the confronting surfaces of the interior of said U-shaped flange forming a portion of a V-bed;
   a rod having a closed distal end and a proximal end and adapted for slidable insertion into said cannula lumen, said rod having a length greater than said cannula;
   a generally planar flange attached to the proximal end of said rod;
   said rod flange including a second mating surface adapted to mate with said first mating surface and including a projection extending from said second mating surface having surfaces forming a second portion of said V-bed and cooperating with said first portion of said V-bed to form an interfitting V-bed for restraining relative rotation between said rod and said cannula and for restraining said rod from receding into said cannula as said trocar is advanced through body tissue during insertion.

2. The trocar of claim 1 wherein said U-shaped flange is disposed in a generally planar configuration aligned generally parallel to but radially offset from the longitudinal axis of said cannula;
   said means for supporting said cannula integral with said U-shaped flange in a radially offset relationship from the plane of said U-shaped flange;
   said second handle second mating surface disposed in a generally planar configuration and aligned generally parallel to said first mating surface of said first handle.

3. The trocar of claim 2 wherein the generally parallel first and second mating surfaces of said first and second handle are adapted for sliding contact to help restrain said rod.

4. The trocar of claim 2 wherein said support for said rod depending from said second handle and said handle is aligned generally parallel to and coaxially with said cannula to facilitate ease of insertion of said rod into and through said cannula.

5. The trocar of claim 1 further including wings on said second mating surface extending beyond said first mating surface to facilitate better gripping of said trocar by a user.

6. The trocar of claim 1 further including a raised portion extending from said second handle adapted for easy gripping by the user to facilitate retraction of said second handle from engagement with said first handle.

7. The trocar of claim 1 wherein the base of said U-shaped flange and the confronting surface of said projection form a stop to control the distance which the distal end of said rod projects beyond the distal end of said cannula when said rod is fully inserted into said cannula.

8. The trocar of claim 1 wherein said rod includes an outer circumferential surface for slidably engaging the interior wall of said cannula lumen so that said rod substantially fills said lumen to inhibit the entry of body tissue into said lumen during trocar insertion.

9. The trocar of claim 1 further including a catheter holder means on said cannula flange for holding a proximal portion of a catheter;
   said distal end of said rod projecting a predetermined distance past the distal end of said cannula when said rod is fully inserted into said cannula to provide means for holding the distal end of a drainage catheter;

said projecting distal end of said rod and said catheter holder providing means for holding a drainage catheter on said trocar entirely outside the lumen of said cannula.

10. The trocar of claim 9 wherein said catheter holder includes a longitudinally-extending slot adapted to removably receive a catheter and to hold a proximal portion thereof.

11. The trocar of claim 1 wherein the axial length of said V-bed is greater than the difference in lengths between said cannula and said rod so that said rod may be retracted into said cannula with said V-bed still in interfitting relationship.

* * * * *